(12) United States Patent
Yan

(10) Patent No.: US 8,968,872 B2
(45) Date of Patent: *Mar. 3, 2015

(54) ENCAPSULATED AGGLOMERATION OF MICROCAPSULES AND METHOD FOR THE PREPARATION THEREOF

(75) Inventor: Nianxi Yan, Halifax (CA)

(73) Assignee: DSM Nutritional Products AG, Kaiseraugst (CH)

( * ) Notice: Subject to any disclaimer, the term of this patent is extended or adjusted under 35 U.S.C. 154(b) by 444 days.

This patent is subject to a terminal disclaimer.

(21) Appl. No.: 12/768,152

(22) Filed: Apr. 27, 2010

(65) Prior Publication Data

US 2010/0209524 A1   Aug. 19, 2010

Related U.S. Application Data

(63) Continuation of application No. 10/891,776, filed on Jul. 15, 2004, now Pat. No. 7,727,629, which is a continuation of application No. 10/120,621, filed on Apr. 11, 2002, now Pat. No. 6,974,592.

(51) Int. Cl.
*B01J 13/02* (2006.01)
*A61K 9/50* (2006.01)
(Continued)

(52) U.S. Cl.
CPC .............. *A23L 1/0029* (2013.01); *A23L 1/3006* (2013.01); *A61K 9/501* (2013.01); *A61K 9/5052* (2013.01);
(Continued)

(58) Field of Classification Search
CPC ........... A61K 8/11; A61K 9/107; B82Y 5/00; A23L 1/03
USPC ................ 428/402.2, 402, 402.1, 402.24; 424/498, 499, 500; 426/648, 601
See application file for complete search history.

(56) References Cited

U.S. PATENT DOCUMENTS 2,800,457 A   7/1957   Green et al.
2,800,458 A   7/1957   Green
(Continued)

FOREIGN PATENT DOCUMENTS

CA   2318539 A1   7/1999
CA   2447002      4/2003
(Continued)

OTHER PUBLICATIONS

Reasons for Submission on behalf of Japan Capsular Products Inc. filed in Japanese Patent Application No. 2003-583137 on Nov. 26, 2010.
(Continued)

*Primary Examiner* — James J Seidleck
*Assistant Examiner* — S. Camilla Pourbohloul
(74) *Attorney, Agent, or Firm* — Meunier Carlin & Curfman, LLC

(57) ABSTRACT

Microcapsules comprising an agglomeration of primary microcapsules, each individual primary microcapsule having a primary shell and the agglomeration being encapsulated by an outer shell, may be prepared by providing an aqueous mixture of a loading substance and a shell material, adjusting pH, temperature, concentration and/or mixing speed to form primary shells of shell material around the loading substance and cooling the aqueous mixture until the primary shells agglomerate and an outer shell of shell material forms around the agglomeration. Such microcapsules are useful for storing a substance and for delivering the substance to a desired environment.

12 Claims, 1 Drawing Sheet

(51) Int. Cl.
*A23L 1/00* (2006.01)
*A23L 1/30* (2006.01)
*B01J 13/10* (2006.01)

(52) U.S. Cl.
CPC .............. *B01J 13/10* (2013.01); *A23V 2002/00* (2013.01); *Y10S 514/962* (2013.01); *Y10S 514/963* (2013.01)
USPC ........ 428/402.2; 424/489; 424/496; 514/962; 514/963

(56) References Cited

U.S. PATENT DOCUMENTS

| | | | |
|---|---|---|---|
| 3,041,289 A | 6/1962 | Katchen et al. | |
| 3,179,600 A * | 4/1965 | Brockett | 503/200 |
| 3,190,837 A | 6/1965 | Brynko | |
| 3,436,355 A | 4/1969 | Bakan et al. | |
| 3,526,682 A | 9/1970 | Timreck | |
| 3,697,437 A | 10/1972 | Fogel et al. | |
| 4,010,038 A | 3/1977 | Iwasaki et al. | |
| 4,217,370 A | 8/1980 | Rawlings et al. | |
| 4,219,439 A | 8/1980 | Miyake et al. | |
| 4,222,891 A | 9/1980 | Okimoto et al. | |
| 4,232,084 A | 11/1980 | Tate | |
| 4,273,672 A | 6/1981 | Vassiliades | |
| 4,442,051 A | 4/1984 | Rowe et al. | |
| 4,485,172 A | 11/1984 | Gierhart | |
| 4,670,247 A | 6/1987 | Scialpi | |
| 4,695,466 A | 9/1987 | Morishita et al. | |
| 4,744,933 A | 5/1988 | Rha et al. | |
| 4,749,620 A | 6/1988 | Rha et al. | |
| 4,808,408 A | 2/1989 | Baker et al. | |
| 4,861,627 A | 8/1989 | Mathiowitz et al. | |
| 4,867,986 A | 9/1989 | Desai et al. | |
| 4,891,172 A | 1/1990 | Matsushita et al. | |
| 4,895,725 A | 1/1990 | Kantor et al. | |
| 4,923,855 A | 5/1990 | Jensen | |
| 4,946,624 A | 8/1990 | Michael | |
| 4,954,492 A | 9/1990 | Jensen | |
| 4,963,367 A | 10/1990 | Ecanow | |
| 5,013,569 A * | 5/1991 | Rubin | 426/585 |
| 5,035,896 A | 7/1991 | Aptel et al. | |
| 5,051,304 A | 9/1991 | David et al. | |
| 5,059,622 A | 10/1991 | Sears | |
| 5,130,061 A | 7/1992 | Cornieri et al. | |
| 5,156,956 A | 10/1992 | Motoki | |
| 5,194,615 A | 3/1993 | Jensen | |
| 5,204,029 A | 4/1993 | Morgan et al. | |
| 5,330,778 A | 7/1994 | Stark | |
| 5,356,636 A | 10/1994 | Schneider | |
| 5,378,413 A | 1/1995 | Mihm et al. | |
| 5,428,014 A | 6/1995 | Labroo | |
| 5,456,985 A | 10/1995 | Zaoulli et al. | |
| 5,573,934 A | 11/1996 | Hubbell et al. | |
| 5,603,952 A | 2/1997 | Soper | |
| 5,603,961 A | 2/1997 | Suzuki et al. | |
| 5,670,209 A | 9/1997 | Wyckoff | |
| 5,700,397 A | 12/1997 | Maeda et al. | |
| 5,759,599 A | 6/1998 | Wampler et al. | |
| 5,766,637 A | 6/1998 | Shine et al. | |
| 5,780,056 A | 7/1998 | Akamatsu et al. | |
| 5,788,991 A | 8/1998 | Natske et al. | |
| 5,827,531 A | 10/1998 | Morrison et al. | |
| 5,855,826 A | 1/1999 | Lee et al. | |
| 5,872,140 A | 2/1999 | Hesse et al. | |
| 5,993,851 A | 11/1999 | Foldvari | |
| 5,997,863 A | 12/1999 | Zimmermann | |
| 6,019,998 A | 2/2000 | Nomoto et al. | |
| 6,020,200 A | 2/2000 | Enevol | |
| 6,039,901 A | 3/2000 | Soper | |
| 6,063,820 A | 5/2000 | Cavazza | |
| 6,103,378 A | 8/2000 | Yao et al. | |
| 6,106,875 A | 8/2000 | Soper et al. | |
| 6,221,401 B1 | 4/2001 | Zasadzinski et al. | |
| 6,234,464 B1 | 5/2001 | Krumbholz et al. | |
| 6,274,174 B1 | 8/2001 | Hom-ma et al. | |
| 6,300,377 B1 | 10/2001 | Chopra | |
| 6,325,951 B1 | 12/2001 | Soper et al. | |
| 6,328,995 B1 | 12/2001 | Bewert | |
| 6,365,176 B1 | 4/2002 | Bell et al. | |
| 6,417,233 B1 | 7/2002 | Sears et al. | |
| 6,441,050 B1 | 8/2002 | Chopra | |
| 6,482,433 B1 | 11/2002 | DeRoos et al. | |
| 6,500,463 B1 * | 12/2002 | van Lengerich | 424/499 |
| 6,528,165 B2 | 3/2003 | Chandler | |
| 6,534,091 B1 | 3/2003 | Garces et al. | |
| 6,534,094 B2 | 3/2003 | Moyano et al. | |
| 6,534,926 B1 | 3/2003 | Miller et al. | |
| 6,544,926 B1 | 4/2003 | Bodmer et al. | |
| 6,630,157 B1 | 10/2003 | Horrobin et al. | |
| 6,652,891 B2 | 11/2003 | Selzer | |
| 6,969,530 B1 | 11/2005 | Curtis et al. | |
| 6,972,592 B2 | 12/2005 | Benware | |
| 6,974,592 B2 | 12/2005 | Yan et al. | |
| 7,727,629 B2 | 6/2010 | Yan | |
| 8,039,030 B2 | 10/2011 | Abril et al. | |
| 2002/0031553 A1 | 3/2002 | Moyano et al. | |
| 2003/0044380 A1 | 3/2003 | Zhu et al. | |
| 2003/0078617 A1 | 4/2003 | Schwartz et al. | |
| 2003/0133886 A1 | 7/2003 | Smith et al. | |
| 2003/0193102 A1 | 10/2003 | Yan | |
| 2004/0106591 A1 | 6/2004 | Pacioretti et al. | |
| 2004/0234601 A1 | 11/2004 | Legrand et al. | |
| 2005/0067726 A1 | 3/2005 | Yan et al. | |
| 2005/0118285 A1 | 6/2005 | Lacoutiere | |
| 2005/0249952 A1 | 11/2005 | Vasishtha et al. | |
| 2007/0027028 A1 | 2/2007 | Pears et al. | |
| 2007/0059340 A1 | 3/2007 | Belloe et al. | |
| 2007/0078071 A1 | 4/2007 | Lee | |
| 2007/0141211 A1 | 6/2007 | Kolar et al. | |
| 2007/0224216 A1 | 9/2007 | Teas | |
| 2009/0274791 A1 | 11/2009 | Mattson | |
| 2010/0055281 A1 | 3/2010 | Barrow | |
| 2010/0173002 A1 | 7/2010 | Yulai et al. | |

FOREIGN PATENT DOCUMENTS

| | | |
|---|---|---|
| DE | 1035319 | 7/1958 |
| EP | 0301777 | 2/1989 |
| EP | 0416575 | 3/1991 |
| EP | 0426428 | 5/1991 |
| EP | 0434760 | 1/1994 |
| EP | 0782833 | 7/1997 |
| EP | 0856355 | 8/1998 |
| EP | 1116516 | 7/2001 |
| EP | 0821881 | 9/2001 |
| EP | 0644771 | 8/2002 |
| EP | 1237423 | 9/2002 |
| EP | 0982038 | 1/2003 |
| EP | 0745670 | 6/2004 |
| EP | 1430947 A1 | 6/2004 |
| EP | 1357977 B1 | 7/2004 |
| EP | 0897970 | 9/2004 |
| GB | 1198412 | 7/1970 |
| GB | 2091286 | 7/1982 |
| GB | 2115768 | 9/1983 |
| JP | 5394273 A | 8/1978 |
| JP | 5828234 | 2/1983 |
| JP | 58149645 | 9/1983 |
| JP | 61172807 | 8/1986 |
| JP | 1148388 | 6/1989 |
| JP | 02086743 | 3/1990 |
| JP | 5292899 | 11/1993 |
| JP | 2005/522313 | 7/2005 |
| WO | WO 91/06287 | 5/1991 |
| WO | WO 92/11083 | 7/1992 |
| WO | WO 97/13416 | 4/1997 |
| WO | WO 97/40701 | 11/1997 |
| WO | WO 01/80656 | 11/2001 |
| WO | WO 02/096408 | 12/2002 |
| WO | WO03086104 A1 | 10/2003 |
| WO | WO 03/105606 | 12/2003 |
| WO | WO 03/106014 | 12/2003 |

(56) References Cited

FOREIGN PATENT DOCUMENTS

| WO | 2004/054702 | 7/2004 |
|---|---|---|
| WO | WO2007054207 A1 | 5/2007 |
| WO | WO2007055815 A1 | 5/2007 |

OTHER PUBLICATIONS

Bohnet et al., Ullmann's Encyclopedia of Industrial Chemistry, vol. II, p. 668, right col. (2003).
Examination report for Application No. 200780019734.2 dated May 6, 2011.
Examination report for Application No. MX/a/2008/012967 dated Apr. 27, 2011.
Examination report for Application No. 200780029069.5 dated Feb. 24, 2011.
Examination report for Application No. 07825594.0 dated Mar. 30, 2011.
Examination report for Application No. 200880007740.0 dated Mar. 23, 2011.
Examination report for Application No. 2003-583137 dated May 10, 2011.
Limmer, "Remington: The Science and Practice of Pharmacy," p. 332, left col. (2000).
Notice of Allowance for U.S. Appl. No. 11/227,961 dated Jun. 14, 2011.
Response to Opposition for Application No. EP06020381.7 dated Jun. 29, 2011.
Examination Report for Application No. 565606 dated May 13, 2010.
Examination Report for Application No. 573327 dated May 28, 2010.
Examination Report for Application No. 573327 dated Nov. 16, 2011.
Examination Report for Application No. 596403 dated Nov. 16, 2011.
Office Action for Application No. 200680032544.X dated Oct. 20, 2011.
Office Action for Application No. 200780019734.2 dated May 6, 2011.
Office Action for Application No. 200780029069.5 dated Feb. 24, 2011.
Office Action for Application No. 200880007740.0 dated Mar. 23, 2011.
Office Action for Application No. 200800269 dated Mar. 18, 2010.
Office Action for Application No. 200800269 dated Jul. 30, 2010.
Office Action for Application No. 07754635.6 dated Dec. 21, 2009.
Office Action for Application No. 07754635.6 dated Aug. 26, 2011.
Office Action for Application No. 07825594.0 dated Mar. 30, 2011.
Office Action for Application No. 08713076.1 dated Sep. 21, 2011.
Office Action for Application No. 2008-520263 dated Feb. 22, 2011.
Office Action for Application No. 7007996/2005 dated Nov. 4, 2011.
Office Action for Application No. MX/a/2008/000210 dated Oct. 20, 2011.
Office Action for U.S. Appl. No. 11/918,150 dated Nov. 16, 2011.
Office Action for U.S. Appl. No. 12/308,045 dated Sep. 9, 2011.
Office Action for U.S. Appl. No. 11/988,320 dated Sep. 1, 2011.
Encyclopedia of Pharmaceutical Technology, "Micoencapsulation," Editors; James Swarbrick and James C. Boylan, Marcel Dekker, Inc., New York, vol. 9, pp. 423-441.
Office Action for Application No. AU 2007282922 dated Mar. 2, 2012.
Office Action for Application No. AU 2007238985 dated Dec. 5, 2011.
Examination Report for Application No. AU 2008205325 dated Jun. 22, 2012.
Examination Report for Application No. CL 2008-63 dated May 15, 2012.
Office Action for Application No. CN 200780019734.2 dated Apr. 25, 2012.
Office Action for Application No. CN 200780029069.5 dated Apr. 27, 2012.
Office Action for Application No. CN 200880007740.0 dated Mar. 16, 2012.
Office Action for Application No. EP 07825594.0 dated Aug. 31, 2011.
Office Action for Application No. EP 07754635.6 dated Dec. 21, 2009.
Office Action for Application No. EP 07754635.6 dated Mar. 6, 2012.
Office Action for Application No. EP 11196119.9 dated Mar. 1, 2012.
Office Action for Application No. EP 06773967.2 dated May 18, 2012.
Examination Report for Application No. JP 2009-523371 dated Sep. 24, 2012.
Examination Report for Application No. JP 2009-545586 dated Sep. 19, 2012.
Office Action for Application No. JP 2003-583137 dated Jan. 24, 2012.
Examination Report for Application No. JP 2003-583137 dated Aug. 24, 2012.
Office Action for Application No. JP 2009-504244 dated Feb. 20, 2011.
Examination Report for Application No. JP 2010-190957 dated Oct. 16, 2012.
Office Action for Application No. KR 10-2011-7022451 dated Dec. 22, 2011.
Office Action for Application No. MX/a/2008/015556 dated Mar. 15, 2012.
Office Action for Application No. MX/a/2008/000210 dated Feb. 20, 2012.
Office Action for Application No. NZ 573327 dated Dec. 8, 2011.
Office Action for Application No. NZ 578872 dated Nov. 11, 2011.
Office Action for Application No. NZ 572529 dated May 21, 2010.
Response to Office Action for NZ 572529 dated Oct. 1, 2010.
Office Action for Application No. NZ 572529 dated Oct. 22, 2010.
Examination Report for Application No. NZ 600903 dated Jul. 3, 2012.
Office Action for Application No. PE 000110-2008 dated Feb. 29, 2012.
Office Action for U.S. Appl. No. 11/435,605 dated Sep. 2, 2010.
Response to Office Action for U.S. Appl. No. 11/435,605 dated Nov. 5, 2010.
Office Action for U.S. Appl. No. 11/435,605 dated Jan. 24, 2011.
Response to Office Action for U.S. Appl. No. 11/435,605 dated Apr. 13, 2011.
Office Action for U.S. Appl. No. 12/308,045 dated Feb. 17, 2012.
Office Action for U.S. Appl. No. 13/009,418 dated Sep. 5, 2012.
Extended European Search Report for Application No. EP 07825594.0 dated Aug. 31, 2011.
Response to Office Action for U.S. Appl. No. 12/308,045 dated Aug. 7, 2012.
Office Action for U.S. Appl. No. 12/308,045 dated Nov. 16, 2012.
Schrooyen et al., Microencapsulation: its application in nutrition, Proceedings of the Nutrition Society, 60:475-479 (2001).
Summons to Attend Oral Proceedings for Application No. EP 03711759.5 dated Jan. 4, 2012.
Summons to Attend Oral Proceedings for Application No. EP 06020381.7 dated Jan. 4, 2012.
Office Action for U.S. Appl. No. 12/522,826 dated Aug. 7, 2012.
Office Action for U.S. Appl. No. 12/522,826 dated Feb. 28, 2013.
Minutes and Decision of Oral Proceeding for Application No. EP 03711759.5 dated Feb. 1, 2003.
Minutes and Decision of Oral Proceeding for Application No. EP 06020381.7 dated Feb. 6, 2003.
Chourpa, Igor, et al., "Conformational Modifications of α Gliadin and Globulin Proteins upon Complex Coacervates Formation with Gum Arabic as Studied by Raman Microspectroscopy," Biomacromolecules, vol. 7, 2006, pp. 2616-2623.
Jizomoto, Hiroaki, "Phase Separation Induced in Gelatin-Base Coacervation Systems by Addition of Water-Soluble Nonionic Polymers I: Microencapsulation," Journal of Pharmaceutical Sciences, vol. 73, No. 7, 1984, pp. 879-882.
Office Action for U.S. Appl. No. 11/988,320 dated Sep. 6, 2013.
Office Action for U.S. Appl. No. 12/308,045 dated Oct. 7, 2013.
Office Action for U.S. Appl. No. 12/522,826 dated Jul. 2, 2013.

(56) References Cited

OTHER PUBLICATIONS

Office Action for U.S. Appl. No. 13/009,418 dated Jun. 21, 2013.
Office Action for Application No. CN 200780029069.5 dated Sep. 24, 2013.
Office Action for Application No. JP 2009523371 dated Oct. 17, 2013.
Office Action for Application No. KR 1020097000087 dated Oct. 18, 2013 (English Translation).
Office Action for Application No. EP 08713076.1 dated Feb. 18, 2013.
Boh et al., "Microcapsule Applications: Patent and Literature Analysis," MML Series, 6:85-156 (2003).
Encyclopedia of Pharmaceutical Technology, "Micoencapsulation," Editors; James Swarbrick and James C. Boylan, Marcel Dekker, Inc., New York, vol. 9, pp. 423-441, Nov. 9, 1993.
Appel et al., "Does supplementation of diet with 'fish oil' reduce blood pressure? A meta-analysis of controlled clinical trials," *Arch Intern Med.*, 153(12):1429-1438 (1993).
Barrow et al., "Stabilization of highly unsaturated fatty acids and delivery into foods," *Lipid Technology*, 9(5):108-111 (2007).
Beestman, "Microencapsulation of Solid Particles," Chemical Abstract, Abstracts of Papers, 220$^{th}$ ACS National Meeting, Washington, DC, United States, Aug. 20-24, 2000, AGRO-037. CODEN: 69FZC3 AN 2000:793223.
Borghi, "Omega-3 LC PUFAs, A new solution for pasteurized milk enrichment," *Wellness Foods Europe*, pp. 25-26 (May 2005).
Calon et al., "Docosahexaenoic acid protects from dentritic pathology in an Alzeheimer's Disease mouse model," *Neuron*, 43:633-645 (2004).
Choi et al., "Physicochemical and sensory characteristics of fish gelatin," *J. Food Sci. Food Chemistry and Toxicology*, 65:194-199 (2000).
Dyrberg et al., "In Omega-3 fatty acids: prevention and treatment of vascular disease," Kristensen et al., Eds. Bi. & Gi Publ., Verona-Springer-Verlag, London, pp. 217-226 (1995).
European Patent Office European Search Report for 06020381.7 dated Apr. 10, 2007.
Fong, "Microencapsulation by solvent and organic phase separation processes," *Controlled Release Systems: Fabrication Technology*, Hsieh Ed., CRC Press, New York, pp. 99-105 (1988).
Gissi-Prevenzione Investigators, "Dietary supplementation with Omega-3 polyunsaturated fatty acids and vitamin E after myocardial infarction: results of the GISSI-Prevenzione trial," *Lancet*, 354:447-455 (1999).
Goyer, "Toxic effects of metals," *Casarett and Doull's Toxicology*, Amdur et al., Eds., 4$^{th}$ ed., Pergamon Press, New York, pp. 638-639 (1991).
Harris, "Extending the cardiovascular benefits of Omega-3 fatty acids," *Curr. Atheroscler Rep.*, 7:375-380 (2005).
Haug et al., "Physical and rheological properties of fish gelatin compared to mammalian gelatin," *Food Hydrocolloids*, 18:203-213 (2004).
Holub, "Clinical Nutrition: 4 Omega-3 fatty acids in cardiovascular care," *CMAJ*, 166(5):608-615 (2002).
http://en.wikipedia.org/wiki/morula, 2011.
http://www.advancedfertility.com/4cell.htm, 1996.
http://www.advancedfertility.com/8cell.htm, 1996.
http://www.advancedfertility.com/morula.htm, 1996.
Ijichi et al., "Multi-Layered GelatinAcacia Microcapsules by Complex Coacervation Method," *J. of Chem Eng. of Japan.*, 30(5):793-798 (1997).
International Search Report and Written Opinion for PCT/US08/000301 mailed Apr. 30, 2008.
International Search Report and Written Opinion for PCT/US07/008138 mailed May 9, 2008.
International Search Report and Written Opinion for PCT/IB07/03358 mailed Apr. 25, 2008.
European Search Authority International Search Report for PCT/IB2006/001214 and Written Opinion mailed Feb. 8, 2007.
International Search Report and Written Opinion for PCT/IB06/01526 mailed Aug. 22, 2006.
Kage et al., "Microencapsulation of mono-dispersed droplets by complex coacervation and membrane thickness of generated capsules," Chemical Abstract No. Accession 615273 (2000).
Kas et al., "Microencapsulation using coacervatoin/phrase separation," In *Handbook of Pharmaceutical Controlled Release Technology*, Wise Ed., Marcel Dekker Inc., New York, pp. 301-328 (2000).
Kris-Etherton et al., "Fish consumption, fish oil, Omega-3 fatty acids and cardiovascular disease," *The American Heart Association Scientific Statement*, 106(21):2747-2757 (Nov. 2002).
Kondo et al., "Microencapsulation utilizing phase separation from an aqueous solution system," *Microcapsule Processing and Technology*, Marcel Dekker Inc., New York, pp. 70-95 (1979).
Leclercq et al., "Formation and characterization of microcapsules by complex coacervation with liquid or solid aroma cores," *Flavour Fragr. J.*, 24:17-24 (2009).
Magdassi et al., "Microencapsulation of Oil-in-Water Emulsions by Proteins," *Microencapsulation—Methods and Industrial Applications*, edited by Simon Benita, Marcel Dekker, Inc., New York, pp. 21-33 (1996).
Marcus et al., "The Vitamins," *Goodman and Gilman's the Pharmacological Basis of Therapeutics*, McGraw-Hill, Inc., New York, pp. 1524-1527 (1990).
Mori et al., "Purified eicosapentaenoic and docosapentaenoic acids have differential effects on serum lipids and lipoproteins, LDL particle size, glucose, and insulin in mildly hypelipidemic men," *Am. J. Clin. Nutr.*, 71:1085-1094 (2000).
Muskiet et al., "Is docosahexaenoic acid (DHA) essential? Lessons from DHA status regulation, our ancient diet, epidemiology and randomized controlled trials," *J. Nutr.*, 134(1):183-186 (2004).
O'Keefe et al., "Omega-3 acids: Time for clinical implementation?" *Am. J. Cardiology*, 85:1239-1241 (20002).
Onuki et al., "In vivo effects of highly purified docosahexaenoic acid on rectal insulin absorption," *Int. J. Pharm.*, 198:147-156 (2000).
Opposition against EP1492417, Aug. 14, 2007.
Ovide-Borodeaux et al., "Docosahexaenoic acid affects insulin-deficiency and insul resistant-induced alterations in cardiac mitochondria," *Am. J. Physiool. Regul. Integr. Comp. Physiol.*, 286:R519-R527 (2003).
Radack et al., "The effects of low doses of Omega-3 fatty acid supplementation on blood pressure in hypertensive subjects: a randomized controlled trial," *Arch. Intern. Med.*, 151:1173-1180 (1991).
Recommended Daily Allowances, Ninth Revised Edition, The Natural Academy of Sciences, p. 160 (1980).
Response to Opposition against EP1492417, Aug. 14, 2007.
Sparks, "Microencapsulation," *Kirk-Othmer, Encyclopedia of Chemical Technology*, vol. 15, 3$^{rd}$ Ed., John Wiley & Sons Inc., New York, pp. 470-793 (1981).
Soper, "Utilization of coacervated flavors," *Encapsulation and Controlled Release of Food Ingredients*, Risch and Reineccius Ed., ACS Symposium Series 590, Washington, D.C., pp. 104-112 (1995).
Sugano et al., "Balanced intake of polyunsaturated fatty acids for health benefits," *J. Oleo. Sci.*, 50(5):305-311 (2001).
Thimma et al., "Study of complex coacervation of gelatin with sodium carboxymethyl guar gum: Microencapsulation of close oil and sulphamethoxazole," *J. Microencapsulation*, 20(2):203-210 (2003).
Webb, "Alternative sources of Omega-3 fatty acids," *Natural Foods Merchandiser*, XXVI(8):40-44 (2005).
Whorton et al., "Evaluation of the mechanisms associated with the release of encapsulated flavor form maltodextrin matrices," *Encapsulation and Controlled Release of Food Ingredients*, Risch and Reineccius Ed., ACS Symposium Series 590, Washington, D.C., pp. 143-160 (1995).
Yoshida et al., "Manufacture of microcapsules from complex coacervation processes," *Chemical Abstract*, Accession No. 140735 (1990).

\* cited by examiner

ENCAPSULATED AGGLOMERATION OF MICROCAPSULES AND METHOD FOR THE PREPARATION THEREOF

CROSS REFERENCE TO RELATED APPLICATIONS

This application is a continuation of and claims the benefit of priority to U.S. application Ser. No. 10/891,776 filed on Jul. 15, 2004, now U.S. Pat. No. 7,727,629, which is a continuation of and claims the benefit of priority to U.S. application Ser. No. 10/120,621 filed on Apr. 11, 2002, now U.S. Pat. No. 6,974,592. Both U.S. application Ser. Nos. 10/891,776 and 10/120,621 are incorporated herein in their entireties by this reference.

FIELD OF THE INVENTION

This invention relates to microcapsules, methods of preparing microcapsules and to their use.

BACKGROUND OF THE INVENTION

Microcapsules are defined as small particles of solids, or droplets of liquids, inside a thin coating of a shell material such as beeswax, starch, gelatine or polyacrylic acid. They are used, for example, to prepare liquids as free-flowing powders or compressed solids, to separate reactive materials, to reduce toxicity, to protect against oxidation and/or to control the rate of release of a substance such as an enzyme, a flavour, a nutrient, a drug, etc.

Over the past fifty years, the prior art has concentrated on so-called "single-core" microcapsules. However, one of the problems with single-core microcapsules is their susceptibility to rupture. To increase the strength of microcapsules, it is known in the art to increase the thickness of the microcapsule wall. However, this leads to a reduction in the loading capacity of the microcapsule. Another approach has been to create so-called "multi-core" microcapsules. For example, U.S. Pat. No. 5,780,056 discloses a "multi-core" microcapsule having gelatine as a shell material. These microcapsules are formed by spray cooling an aqueous emulsion of oil or carotenoid particles such that the gelatine hardens around "cores" of the oil or carotenoid particles. Yoshida et al. (Chemical Abstract 1990:140.735 or Japanese patent publication JP 01-148338 published Jun. 9, 1989) discloses a complex coacervation process for the manufacture of microcapsules in which an emulsion of gelatine and paraffin wax is added to an arabic rubber solution and then mixed with a surfactant to form "multi-core" microcapsules. Ijichi et al. (*J. Chem. Eng. Jpn.* (1997) 30(5):793-798) microencapsulated large droplets of biphenyl using a complex coacervation process to form multilayered microcapsules. U.S. Pat. Nos. 4,219,439 and 4,222,891 disclose "multi-nucleus", oil-containing microcapsules having an average diameter of 3-20 µm with an oil droplet size of 1-10 µm for use in pressure-sensitive copying papers and heat sensitive recording papers. While some improvement in the strength of microcapsules may be realized by using methods such as these, there remains a need for microcapsules having good rupture strength and good oxidative barrier to the encapsulated substance, preferably in conjunction with high load volumes. Illustrative of this need is the current lack of commercially available 'multicore' microcapsules.

SUMMARY OF THE INVENTION

There is provided a microcapsule comprising an agglomeration of primary microcapsules, each individual primary microcapsule having a primary shell and the agglomeration being encapsulated by an outer shell.

There is further provided a process for preparing microcapsules, the process comprising:
(a) providing an aqueous mixture of a loading substance, a first polymer component of shell material and a second polymer component of shell material;
(b) adjusting pH, temperature, concentration, mixing speed or a combination thereof to form shell material comprising the first and second polymer components, the shell material forming primary shells around the loading substance;
(c) cooling the aqueous mixture to a temperature above gel point of the shell material until the primary shells form agglomerations; and,
(d) further cooling the aqueous mixture to form an outer shell of shell material around the agglomerations.

There is still further provided a process for preparing microcapsules, the process comprising:
(a) providing an aqueous mixture of a first polymer component of shell material;
(b) dispersing a loading substance into the aqueous mixture;
(c) then adding a second polymer component of shell material to the aqueous mixture;
(d) adjusting pH, temperature, concentration, mixing speed or a combination thereof to form shell material comprising complex coacervates of the first and second polymer components, the shell material forming primary shells around the loading substance;
(e) cooling the aqueous mixture to a temperature above gel point of the shell material until the primary shells form agglomerations; and,
(f) further cooling the aqueous mixture to form an outer shell of shell material around the agglomerations.

Microcapsules of the present invention may be used to contain a loading substance for a variety of applications.

DETAILED DESCRIPTION

Composition

Figure 1:
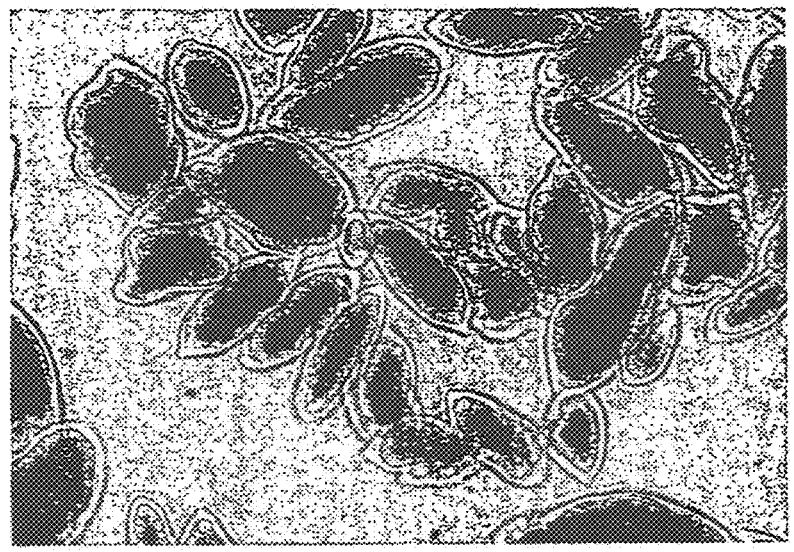
FIG. 1 is an optical micrograph (400×) of encapsulated agglomerations of microcapsules in accordance with the invention.

The loading substance may be virtually any substance that is not entirely soluble in the aqueous mixture. Preferably, the loading substance is a solid, a hydrophobic liquid, or a mixture of a solid and a hydrophobic liquid. The loading substance is more preferably a hydrophobic liquid, such as grease, oil or a mixture thereof. Typical oils may be fish oils, vegetable oils, mineral oils, derivatives thereof or mixtures thereof. The loading substance may comprise a purified or partially purified oily substance such as a fatty acid, a triglyceride or a mixture thereof. Omega-3 fatty acids, such as α-linolenic acid (18:3n3), octadecatetraenoic acid (18:4n3), eicosapentaenoic acid (20:5n3) (EPA) and docosahexaenoic acid (22:6n3) (DHA), and derivatives thereof and mixtures thereof, are preferred. Many types of derivatives are well known to one skilled in the art. Examples of suitable derivatives are esters, such as phytosterol esters, branched or unbranched $C_1$-$C_{30}$ alkyl esters, branched or unbranched $C_2$-$C_{30}$ alkenyl esters or branched or unbranched $C_3$-$C_{30}$ cycloalkyl esters, in particular phytosterol esters and $C_1$-$C_6$ alkyl esters. Preferred sources of oils are oils derived from aquatic organisms (e.g. anchovies, capelin, Atlantic cod, Atlantic herring, Atlantic mackerel, Atlantic menhaden, salmonids, sardines, shark, tuna, etc) and plants (e.g. flax, vegetables, algae, etc). While the loading substance may or may not be a biologically active substance, the microcapsules of the present invention are particularly suited for biologically active substances, for example, drugs, nutritional supplements, flavours or mixtures thereof. Particularly preferred loading substances include antioxidants, such as $CoQ_{10}$ and vitamin E.

The shell material may be any material that can form a microcapsule around the loading substance of interest. The shell material typically comprises at least one polymer component. Examples of polymer components include, but are not limited to, gelatines, polyphosphate, polysaccharides and mixtures thereof. Preferred polymer components are gelatine A, gelatine B, polyphosphate, gum arabic, alginate, chitosan, carrageenan, pectin, carboxymethylcellulose (CMC) or a mixture thereof. A particularly preferred form of gelatine type A has a Bloom strength of 50-350, more preferably a Bloom strength of 275.

The shell material is preferably a two-component system made from a mixture of different types of polymer components. More preferably, the shell material is a complex coacervate between two or more polymer components. Component A is preferably gelatine type A, although other polymers are also contemplated as component A. Component B is preferably gelatine type B, polyphosphate, gum arabic, alginate, chitosan, carrageenan, pectin, carboxymethyl cellulose or a mixture thereof. The molar ratio of component A:component B that is used depends on the type of components but is typically from 1:5 to 15:1. For example, when gelatine type A and polyphosphate are used as components A and B respectively, the molar ratio of component A:component B is preferably 8:1 to 12:1; when gelatine type A and gelatine type B are used as components A and B respectively, the molar ratio of component A:component B is preferably 2:1 to 1:2; and when gelatine type A and alginate are used as components A and B respectively, the molar ratio of component A:component B is preferably 3:1 to 5:1.

Processing aids may be included in the shell material. Processing aids may be used for a variety of reasons. For example, they may be used to promote agglomeration of the primary microcapsules, control microcapsule size and/or to act as an antioxidant. Antioxidant properties are useful both during the process (e.g. during coacervation and/or spray drying) and in the microcapsules after they are formed (i.e. to extend shelf-life, etc). Preferably a small number of processing aids that perform a large number of functions is used. For example, ascorbic acid or a salt thereof may be used to promote agglomeration of the primary microcapsules, to control microcapsule size and to act as an antioxidant. The ascorbic acid or salt thereof is preferably used in an amount of about 100 ppm to about 10,000 ppm, more preferably about 1000 ppm to about 5000 ppm. A salt of ascorbic acid, such as sodium or potassium ascorbate, is particularly preferred in this capacity.

Figure 2:
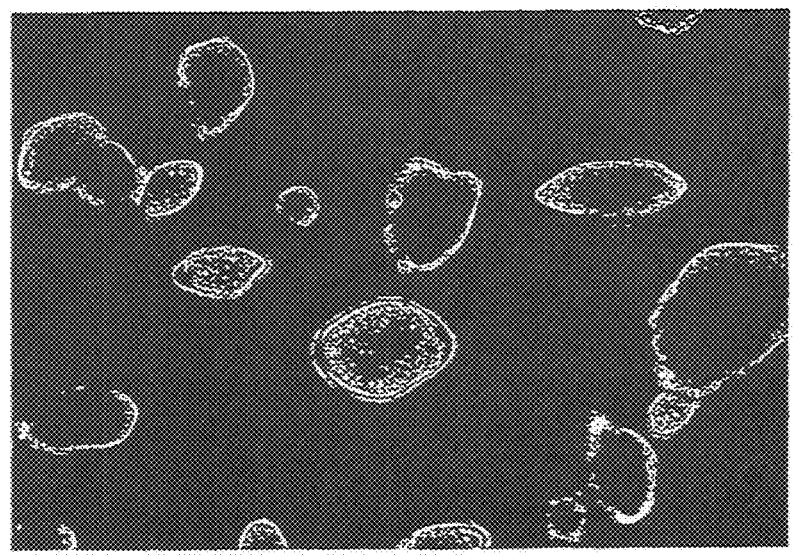
FIG. 2 is a second optical micrograph (400×) of encapsulated agglomerations of microcapsules in accordance with the invention.

The structure of encapsulated agglomerations of microcapsules in accordance with the present invention may be seen in FIGS. 1 and 2, which show that smaller (primary) microcapsules have agglomerated together and that the agglomeration is surrounded by shell material to form a larger microcapsule. Each individual primary microcapsule has its own distinct shell called the primary shell. Furthermore, any space that there may be between the smaller microcapsules is filled with more shell material to hold and surround the smaller microcapsules thereby providing an extremely strong outer shell of the larger microcapsule in addition to the primary shell that forms the smaller microcapsules within the larger microcapsule. In one sense, the encapsulated agglomeration of microcapsules may be viewed as an agglomeration of walled bubbles suspended in a matrix of shell material, i.e. a "foam-like" structure. Such an encapsulated agglomeration of microcapsules provides a stronger, more rupture-resistant structure than is previously known in the art, in conjunction with achieving high loads of loading substance.

The primary microcapsules (primary shells) typically have an average diameter of about 40 nm to about 10 μm, more particularly from about 0.1 μm to about 5 μm, even more particularly about 1 μm. The encapsulated agglomerations (outer shells) may have an average diameter of from about 1 μm to about 2000 μm, more typically from about 20 μm to about 1000 μm, more particularly from about 20 μm to about 100 μm, even more particularly from about 50 μm to about 100 μm.

The encapsulated agglomerations of microcapsules prepared by a process of the present invention typically have a combination of payload and structural strength that are better than multi-core microcapsules of the prior art. For example, payloads of loading substance can be as high as about 70% by weight in microcapsules of the present invention having an average size of about 50 μm for the outer shells and an average size of about 1 μm for the primary shells.

Process:

In the process for preparing microcapsules, an aqueous mixture of a loading substance, a first polymer component of the shell material and a second polymer component of the shell material is formed. The aqueous mixture may be a mechanical mixture, a suspension or an emulsion. When a liquid loading material is used, particularly a hydrophobic liquid, the aqueous mixture is preferably an emulsion of the loading material and the polymer components.

In a more preferred aspect, a first polymer component is provided in aqueous solution, preferably together with processing aids, such as antioxidants. A loading substance may then be dispersed into the aqueous mixture, for example, by using a homogenizer. If the loading substance is a hydrophobic liquid, an emulsion is formed in which a fraction of the first polymer component begins to deposit around individual droplets of loading substance to begin the formation of primary shells. If the loading substance is a solid particle, a suspension is formed in which a fraction of the first polymer component begins to deposit around individual particles to begin the formation of primary shells. At this point, another aqueous solution of a second polymer component may be added to the aqueous mixture.

Droplets or particles of the loading substance in the aqueous mixture preferably have an average diameter of less than 100 μm, more preferably less than 50 μm, even more preferably less than 25 μm. Droplets or particles of the loading substance having an average diameter less than 10 μm or less than 5 μm or less than 3 μm or less than 1 μm may be used. Particle size may be measured using any typical equipment known in the art, for example, a Coulter™ LS230 Particle Size Analyzer, Miami, Fla., USA.

The amount of the polymer components of the shell material provided in the aqueous mixture is typically sufficient to form both the primary shells and the outer shells of the encapsulated agglomeration of microcapsules. Preferably, the loading substance is provided in an amount of from about 1% to about 15% by weight of the aqueous mixture, more preferably from about 3% to about 8% by weight, and even more preferably about 6% by weight.

The pH, temperature, concentration, mixing speed or a combination thereof is then adjusted to accelerate the formation of the primary shells around the droplets or particles of the loading substance. If there is more than one type of polymer component, complex coacervation will occur between the components to form a coacervate, which further deposits around the loading substance to form primary shells of shell material. The pH adjustment depends on the type of shell material to be formed. For example, when gelatine type A is a polymer component, the pH may be adjusted to a value from 3.5-5.0, preferably from 4.0-5.0. If the pH of the mixture starts in the desired range, then little or no pH adjustment is required. The initial temperature of the aqueous mixture is preferably set to a value of from about 40° C. to about 60° C., more preferably at about 50° C. Mixing is preferably adjusted so that there is good mixing without breaking the microcapsules as they form. Particular mixing parameters depend on the type of equipment being used. Any of a variety of types of mixing equipment known in the art may be used. Particularly useful is an axial flow impeller, such as Lightnin™ A310 or A510.

The aqueous mixture may then be cooled under controlled cooling rate and mixing parameters to permit agglomeration of the primary shells to form encapsulated agglomerations of primary shells. The encapsulated agglomerations are discrete particles themselves. It is advantageous to control the formation of the encapsulated agglomerations at a temperature above the gel point of the shell material, and to let excess shell material form a thicker outer shell. It is also possible at this stage to add more polymer components, either of the same kind or a different kind, in order to thicken the outer shell and/or produce microcapsules having primary and outer shells of different composition. The temperature is preferably lowered at a rate of 1° C./10 minutes until it reaches a temperature of from about 5° C. to about 10° C., preferably about 5° C. The outer shell encapsulates the agglomeration of primary shells to form a rigid encapsulated agglomeration of microcapsules.

At this stage, a cross-linker may be added to further increase the rigidity of the microcapsules by cross-linking the shell material in both the outer and primary shells and to make the shells insoluble in both aqueous and oily media. Any suitable cross-linker may be used and the choice of cross-linker depends somewhat on the choice of shell material. Preferred cross-linkers are enzymatic cross-linkers (e.g. transglutaminase), aldehydes (e.g. formaldehyde or gluteraldehyde), tannic acid, alum or a mixture thereof. When the microcapsules are to be used to deliver a biologically active substance to an organism, the cross-linkers are preferably non-toxic or of sufficiently low toxicity. The amount of cross-linker used depends on the type of shell material and may be adjusted to provide more or less structural rigidity as desired. For example, when gelatine type A is used in the shell material, the cross-linker may be conveniently used in an amount of about 1.0% to about 5.0%, preferably about 2.5%, by weight of the gelatine type A. In general, one skilled in the art may routinely determine the desired amount in any given case by simple experimentation.

Finally, the microcapsules may be washed with water and/or dried to provide a free-flowing powder. Drying may be accomplished by a number of methods known in the art, such as freeze drying, drying with ethanol or spray drying. Spray drying is a particularly preferred method for drying the microcapsules. Spray drying techniques are disclosed in "Spray Drying Handbook", K. Masters, 5th edition, Longman Scientific Technical UK, 1991, the disclosure of which is hereby incorporated by reference.

Uses:

The microcapsules produced by the process of the present invention may be used to prepare liquids as free-flowing powders or compressed solids, to store a substance, to separate reactive substances, to reduce toxicity of a substance, to protect a substance against oxidation, to deliver a substance to a specified environment and/or to control the rate of release of a substance. In particular, the microcapsules may be used to deliver a biologically active substance to an organism for nutritional or medical purposes. The biologically active substance may be, for example, a nutritional supplement, a flavour, a drug and/or an enzyme. The organism is preferably a mammal, more preferably a human. Microcapsules containing the biologically active substance may be included, for example, in foods or beverages or in drug delivery systems. Use of the microcapsules of the present invention for formulating a nutritional supplement into human food is particularly preferred.

Microcapsules of the present invention have good rupture strength to help reduce or prevent breaking of the microcapsules during incorporation into food or other formulations. Furthermore, the microcapsule's shells are insoluble in both aqueous and oily media, and help reduce or prevent oxidation and/or deterioration of the loading substance during preparation of the microcapsules, during long-term storage, and/or during incorporation of the microcapsules into a formulation vehicle, for example, into foods, beverages, nutraceutical formulations or pharmaceutical formulations.

EXAMPLES

Example 1

54.5 grams gelatine 275 Bloom type A (isoelectric point of about 9) was mixed with 600 grams of deionized water containing 0.5% sodium ascorbate under agitation at 50° C. until completely dissolved. 5.45 grams of sodium polyphosphate was dissolved in 104 grams of deionized water containing 0.5% sodium ascorbate. 90 grams of a fish oil concentrate containing 30% eicosapentaenoic acid ethyl ester (EPA) and 20% docosahexaenoic acid ethyl ester (DHA) (available from Ocean Nutrition Canada Ltd.) was dispersed with 1.0% of an antioxidant (blend of natural flavour, tocopherols and citric acid available as Duralox™ from Kalsec™) into the gelatine solution with a high speed Polytron™ homogenizer. An oil-in-water emulsion was formed. The oil droplet size had a narrow distribution with an average size of about 1 µm measured by Coulter™ LS230 Particle Size Analyzer. The emulsion was diluted with 700 grams of deionized water containing 0.5% sodium ascorbate at 50° C. The sodium polyphosphate solution was then added into the emulsion and mixed with a Lightnin™ agitator at 600 rpm. The pH was then adjusted to 4.5 with a 10% aqueous acetic acid solution. During pH adjustment and the cooling step that followed pH adjustment, a coacervate formed from the gelatine and polyphosphate coated onto the oil droplets to form primary microcapsules. Cooling was carried out to above the gel point of the gelatine and polyphosphate and the primary microcapsules started to agglomerate to form lumps under agitation. Upon further cooling of the mixture, polymer remaining in the aqueous phase further coated the lumps of primary microcapsules to form an encapsulated agglomeration of microcapsules having an outer shell and having an average size of 50 µm. Once the temperature had been cooled to 5° C., 2.7 grams of 50% gluteraldehyde was added into the mixture to further strengthen the shell. The mixture was then warmed to room temperature and kept stirring for 12 hours. Finally, the microcapsule suspension washed with water. The washed suspension was then spray dried to obtain a free-flowing powder. A payload of 60% was obtained.

Example 2

Encapsulated agglomerations of microcapsules were formed in accordance with the method of Example 1 except that 0.25% sodium ascorbate was used. A payload of 60% was obtained.

Example 3

Encapsulated agglomerations of microcapsules were formed in accordance with the method of Example 1 except that no ascorbate was used. A payload of 60% was obtained.

Example 4

Encapsulated agglomerations of microcapsules were formed in accordance with the method of Example 1 except that 105 grams of fish oil concentrate was used and a payload of 70% was obtained.

Example 5

Encapsulated agglomerations of microcapsules were, formed in accordance with the method of Example 1 except that it was applied to triglyceride (TG) fish oil (available from Ocean Nutrition Canada Ltd.) rather than ethyl ester fish oil.

Example 6

Encapsulated agglomerations of microcapsules were formed in accordance with the method of Example 1 except that gelatine (type A) and gum arabic were used as polymer components of the shell material.

Example 7

Encapsulated agglomerations of microcapsules were formed in accordance with the method of Example 1 except that 150 Bloom gelatine (type A) and polyphosphate were used as polymer components of the shell material and 105 grams of fish oil concentrate was used to obtain a payload of 70%.

Example 8

Encapsulated agglomerations of microcapsules were formed in accordance with the method of Example 1 except that transglutaminase was used to cross-link the shell material.

Example 9

Evaluation of Microcapsules

The microcapsules of Examples 1-8 were evaluated for mechanical strength, encapsulated oil quality and oxidative stability.

Microcapsule shell strength was evaluated by centrifuging a given amount of the prepared microcapsule powders from each of the Examples 1-8 at 34,541 g at 25° C. for 30 minutes in a Sorvall™ Super T-21 centrifuge. The original and the centrifuged powders were washed with hexane to extract oil released from the microcapsules due to shell breakage under centrifuge force. The ratio of percent free oil of the centrifuged powders to that of the original powders is used as an indicator of the shell strength. The lower the ratio, the stronger is the microcapsule's shell.

Oil quality in microcapsules was evaluated by crushing the shells of the prepared microcapsule powders from each of Examples 1-8 with a grinder. The encapsulated oil was then extracted with hexane. Peroxide Value (PV) was analyzed with American Oil Chemist Society Method (AOCS Official Method Cd 8-53: Peroxide value). A high PV indicates a higher concentration of primary oxidation products in the encapsulated oil.

Accelerated oxidative stability was evaluated by placing the prepared microcapsule powders from each of Examples 1-8 in an oxygen bomb (Oxipres™, MIKROLAB AARHUS A/S, Denmark) with an initial oxygen pressure of 5 bar at a constant temperature of 65° C. When the encapsulated fish oil started to oxidize, the oxygen pressure dropped. The time at which the oxygen pressure started to drop is called Induction Period. A longer Induction Period means that the contents of the microcapsules are better protected towards oxidation.

Results are shown in Table 1. The results indicate that the agglomerated microcapsules prepared in accordance with the present invention have excellent strength and resistance to oxidation of the encapsulated loading substance.

TABLE 1

| run # | load (%) | ascorbate (%) | induct period (hr) | PV value | free oil ratio | notes |
|---|---|---|---|---|---|---|
| 1 | 60 | 0.50 | 38 | 3.0 | 2.0 | |
| 2 | 60 | 0.25 | 34 | 4.1 | 1.5 | |
| 3 | 60 | 0.0 | 26 | 7.8 | 1.5 | |
| 4 | 70 | 0.50 | 38 | 3.2 | 1.7 | |
| 5 | 60 | 0.50 | 37 | 0.28 | 3.0 | TG oil |
| 6 | 60 | 0.50 | 30 | 3.4 | 1.5 | gum arabic |
| 7 | 70 | 0.50 | 38 | 4.4 | 2.2 | 150 bloom gelatin |
| 8 | 60 | 0.50 | 33 | 3.2 | 1.1 | enzymatic cross linking |

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The invention claimed is:
1. A process for preparing a microcapsule, the process comprising:
(a) providing an aqueous mixture comprising (i) a biologically active loading substance and (ii) a first and a second polymer component;
(b) adjusting pH, temperature, concentration, mixing speed or a combination thereof of the aqueous mixture to produce a shell material by complex coacervation of only the first and second polymer components, the shell material forming a primary shell around the loading substance, thereby producing a primary microcapsule;

(c) cooling the aqueous mixture until a plurality of the primary microcapsules form an agglomeration;

(d) further cooling the aqueous mixture to produce an outer shell of the shell material by complex coacervation of the first and second polymer components around the agglomeration; and (e) spray drying the aqueous mixture, to produce the microcapsule, wherein the first polymer component is gelatin and the second polymer component is polyphosphate and the microcapsule has not been crosslinked.

2. The method of claim 1, further comprising step (f), adding the microcapsule to a food or beverage.

3. The method of claim 1, wherein the loading substance comprises omega-3 fatty acids, derivatives thereof, or mixtures thereof.

4. The method of claim 3, wherein the loading substance comprises a triglyceride of an omega-3 fatty acid, an ethyl ester of an omega-3 fatty acid, or a phytosterol ester of an omega-3 fatty acid.

5. The method of claim 1, wherein the loading substance is from 60 to 70% by weight of the microcapsule.

6. The method of claim 1, wherein the outer shell has an average diameter of from about 50 µm to about 100 µm.

7. The method of claim 1, wherein the outer shell has an average diameter of from about 20 µm to about 100 µm.

8. The method of claim 1, wherein the primary shell has an average diameter of from about 40 nm to about 10 µm.

9. The method of claim 1, wherein the primary shell has an average diameter of from about 0.1 µm to about 5 µm.

10. The method of claim 1, wherein the primary shell has an average diameter of from about 1 µm to about 5 µm.

11. The method of claim 1, wherein the primary shell has an average diameter of about 1 µm.

12. The method of claim 1, wherein the loading substance further comprises ascorbic acid or a salt thereof.

* * * * *